United States Patent [19]
Khalil et al.

[11] Patent Number: 5,244,630
[45] Date of Patent: * Sep. 14, 1993

[54] DEVICE FOR PERFORMING SOLID-PHASE DIAGNOSTIC ASSAY

[75] Inventors: Omar S. Khalil; Charles F. Hanna, both of Libertyville; Denise G. Huff, Prospect Heights; Thomas F. Zurek, River Forest, all of Ill.

[73] Assignee: Abbott Laboratories, Abbott Park, Ill.

[*] Notice: The portion of the term of this patent subsequent to Apr. 9, 2008 has been disclaimed.

[21] Appl. No.: 425,651

[22] Filed: Oct. 23, 1989

Related U.S. Application Data

[63] Continuation-in-part of Ser. No. 184,726, Apr. 22, 1988, Pat. No. 5,006,309.

[51] Int. Cl.$^5$ ............... G01N 1/28; G01N 33/543
[52] U.S. Cl. ............................ 422/52; 422/56; 422/58; 422/82.05; 422/101; 436/178; 436/180; 435/291; 435/805
[58] Field of Search ............... 422/52, 53, 56, 58, 422/82.05, 101; 435/291, 805; 436/178, 180

[56] References Cited

U.S. PATENT DOCUMENTS

| | | | |
|---|---|---|---|
| 3,997,404 | 12/1976 | Waders | 435/291 |
| 4,246,339 | 1/1981 | Cole et al. | 422/101 |
| 4,396,579 | 8/1983 | Schroeder et al. | 422/52 |
| 4,923,680 | 5/1990 | Nelson | 422/101 |
| 4,999,163 | 3/1991 | Lennon et al. | 422/56 |
| 5,006,309 | 4/1991 | Khalil et al. | 422/58 |

Primary Examiner—James C. Housel
Assistant Examiner—N. Bhat
Attorney, Agent, or Firm—Frank S. Ungemach; Priscilla E. Porembski; Daniel W. Collins

[57] ABSTRACT

A disposable device suitable for performing automated solid-phase diagnostic assays which employs microparticles to complex an analyte and where the microparticle complex becomes retained and immobilized on a fibrous matrix such that the presence of analyte on the microparticles can be detached by optical means. A device is disclosed having a plurality of well pairs comprising a sample well for receiving a sample and reagents for forming a reaction mixture, a read well comprising (a) an entrance port and holder for receiving and holding a quantity of sample and assay reagents, (b) a fibrous matrix for retaining and immobilizing microparticle/analyte complexes for detection, said fibrous matrix positioned below said holder, and having an average spatial separation of fibers greater than the average diameter of said microparticles, (c) absorbent material positioned below said fibrous matrix for assisting the flow of sample and assay reagents through said fibrous matrix, (d) walls or ribs for creating a substantially light-tight real surrounding the wells, (e) a vent for venting air entrapped in the absorbent material and which is displaced by fluids absorbed therein, and (f) a passage between the sample well and the read well whereby sample and reaction mixtures can be transferred and washed from said sample well into said read well without being contacted by any apparatus.

9 Claims, 7 Drawing Sheets

DEVICE FOR PERFORMING SOLID-PHASE DIAGNOSTIC ASSAY

This application is a continuation-in-part of Ser. No. 07/184,721 filed on Apr. 22, 1988, now U.S. Pat. No. 5,006,309.

BACKGROUND OF THE INVENTION

The present invention is directed toward a method and a disposable device for use in an automated solid-phase diagnostic assay. The device is designed to have a plurality of two well pairs, one of each well pairs is where a sample material can be incubated with reagents to perform a solid-phase assay and another in which the results can be read. The reaction mixture is transferred from the first well, the incubation well, to the second well, the read well by a non-contact means using jets of fluid to move the reactants between the two wells. The disposable device has surface features surrounding each well pair that mates with a chemiluminescent reader head in such a way that a light-tight seal is created to allow low-light level measurements. Associated also with each well pair a means for immobilizing and retaining the reaction products, a means for removal of excess reactants and wash solutions and a vent hole to vent air displaced by fluids added into the device.

Techniques for performing an immunoassay are generally known in the art. For example, conventional enzyme immunoassay procedures involve a series of steps wherein an analyte in sample material is initially bound to a corresponding antigen or antibody reagent. A second antigen or antibody is then introduced into the sample which has been labeled with an enzyme or other substance capable of being detected directly or after addition of a suitable reagent such as a chromogenic or fluorogenic substrate or a trigger solution for activating chemiluminescence. The generated signal is then read to indicate the absence or presence of the antigen or the antibody in the sample.

Solid phase immunoassay procedures are preferred over other diagnostic methods because of their specificity and sensitivity as interfering substances can washed away before optical readout.

One form of a conventional solid-phase immunoassay is a "sandwich assay" which involves contacting a test sample suspected of containing an antibody or antigen with a material which has attached to it a protein or another substance capable of binding the antigen or the antibody to the surface of the support. After the antibody or antigen is bound to the support material it is treated with a second antigen or antibody, which is conjugated with an enzyme, a fluorophore or a chemiluminescent label. The second antigen or antibody then becomes bound to the corresponding antibody or antigen on the support. Following one or more washing steps to remove any unbound material in an enzyme immunoassay, an indicator substance, for example, a chromogenic substrate, is added which reads with the enzyme to produce a color change. The color change can be observed visually or more preferably by an instrument to indicate the presence or absence of the antibody or antigen in the sample. For solid-phase fluorescence or chemiluminescence immunoassays, fluorescent labeled moieties can be monitored by using excitation at an appropriate wavelength, while chemiluminescent labeled antigens or antibodies can be followed after reaction by chemically activating the chemiluminescent labels to generate light which can be detected by photometric means.

Many procedures and apparatus have been designed to perform solid-phase immunoassays. U.S. Pat. No. 4,632,910 discloses an apparatus having a porous filter containing a bound receptor for complexing an analyte. In this apparatus an absorbent material is positioned below the porous filter to assist the fluid sample in flowing through the filter. A labeled antibody is then added to the porous filter to detect the presence or absence of the analyte. This approach leads to assays with limited sensitivities as the sample and conjugate incubation takes place on the same matrix. None-specific binding of the sample and conjugate to the porous matrix can occur and contribute to the background of the assay and limits its sensitivity.

In another approach, European Patent Application No. 0131934 discloses an assay device having a plurality of aligned adjacent incubation wells located on its top surface which empty through a filter membrane located above a waste reservoir. U.S. Pat. No. 4,652,533 discloses an assay method using such a device. A solid-phase fluorescent immunoassay reaction mixture is placed in the well and drawn through the membrane by applying reduced pressure to the waste reservoir to separate a solid-phase reaction product from a liquid-phase reactants so that the solid-phase reaction product can be observed. This approach, however, has serious limitations. First, it is limited to use of microparticles as a capture phase. Secondly, the sample, conjugate and microparticles are incubated in the same incubation well that the optical reading takes place. Non-specific binding of sample and conjugate, labeled antigen or antibody, to the membrane filter in the reading well and the wall of the well can occur and contribute to the background of the assay and thus limits its sensitivity. Third, because of using a common vacuum manifold to a plurality of filters, a pinhole in one of the wells will lead to air leaking through this well and no filteration for other wells in the disposable reaction tray. Thirdly, such a disposable device cannot be used for chemiluminescence immunoassay measurements where extreme light tight conditions around each well are required. Other microparticles vacuum filteration devices for immunoassays are available commercially such as Millititer ® Plate from Millipore Corporation, Bedford, Mass.

Other methods for performing a solid-phase immunoassay are disclosed in U.S. Pat. Nos. 4,587,102, and 4,552,839, and European Patent Application 0200381. These references generally disclose procedures for employing particles having a receptor to bind an analyte which is subsequently labeled and deposited on a matrix or other support system. The particles complex is treated with an indicator substance to indicate the presence or absence of an analyte.

While many immunoassay procedures and devices have proved useful, better procedures and devices are continually being sought to improve reliability, efficiency and sensitivity. The present invention provides all of these improvements.

SUMMARY OF THE INVENTION

In one aspect, the present invention is directed toward a device suitable for performing an automated solid-phase diagnostic assay. The ability to perform an automated assay contributes to increased reliability and efficiency.

The device of the present invention comprises a plurality of well pairs, one well of each well pair is a shallow incubation well in which a sample material can be treated with reagents to perform a solid-phase assay and the other well is a read well for retaining and immobilizing the formed immune complex, and in which the results of the immunochemical reaction can be read. The device is designed to allow for the transfer of the sample and reagent mixture from the shallow sample incubation well to the read well via a communicating passage. Separating the incubation well from the read well decreases the possibility of non-specific binding of the sample components in the read well and improves assay sensitivity. The separation and read well has an entrance port and a means for holding a quantity of sample and reagent mixtures positioned over a fibrous matrix which retains and immobilizes the resultant immune complexes. The fibrous matrix is composed of fibers having an average spatial separation greater than 5 microns. Separation of the immune complex on the porous element can be affected by using latex microparticles with antibodies or antigens immobilized on its surface as the capturing solid phase and separating them from the reaction mixture by their physical adhesion to the fibrous pad. Microparticles used in this process have diameters smaller than the spatial separation between the fibers of the pad.

Another preferred method of separation is that which is described in co-pending U.S. patent application Ser. No. 150,278 (filed Jan. 29, 1988) and U.S. patent application Ser. No. 375,029 (filed Jul. 7, 1989), both of which are incorporated by reference herein, directed to the use of ion capture separation wherein the fiber pad is treated with a cationic detergent to render the fibers positively charged. The antibody, or antigen, for the assay in question is chemically attached to a polyanionic acid such as polyglutamic acid or polyacrylic acid. Separation of the immunochemical reaction product will be affected by the electrostatic interaction between the positively charged pad and the negatively charged poly-anion/ immune complex.

The read well further comprises a fluid removal means positioned below the fibrous matrix to enhance the flow of sample and assay reaction mixtures through the fibrous matrix. A preferred means of fluid removal is the use of an absorbant pad in intimate contact with the fibrous matrix.

The present invention also provides for a method of manipulating reaction mixtures without physically contacting the reaction mixture with a pipette tip or other mechanically transfer means. Thus contamination of the assay and apparatus is avoided which increases the sensitivity and accuracy of the assay. This is achieved by washing away the reaction mixture from the shallow incubation well into the read well by injecting wash solution into the incubation well from a series of nozzles at high speed. Injectors are directed at a specific angle to the shallow incubation well.

Another preferred embodiment of this invention is to use such device for performing chemiluminescence immunoassays. Thus the disposable device of the present invention has molded surface features surrounding each incubation well/read well pair that mates with a chemiluminescent detector in such a way that a light-tight seal is created to allow low-light level measurements for high sensitivity assays. Associated with each incubation well/read well pair in the disposable device is a hole to vent the air originally entrapped in the absorbant pad and is displaced by the reaction mixture and wash solutions.

The present invention also provides various methods for performing a solid-phase assay in the device using either microparticle or ion capture separation techniques. In the following example the term capture agent will be used to describe microparticles coated with an immunochemical reactant or a polyanion attached to an immunochemical reactant. In the former case the fibrous pad may be treated with substances that facilitate adherence to the microparticles and flow of the remaining fluids. In the latter case the fibrous pad will be treated with cationic materials that facilitate attachment of the polyanion-immunoreactant complex to the matrix.

One method for performing a sandwich immunoassay in accordance with the invention comprises the following steps:

a) incubating the sample material with an analyte specific conjugate in the shallow incubation well to form an analyte/conjugate complex;

b) simultaneously adding a capture agent to act as a solid phase, incubating the reaction mixture for a time period and at a temperature that maximize the formation of the immune complex and then washing the capture agent/analyte/conjugate complex into the read well.

c) adding additional wash solution to the read well to transfer the capture agent analyte/conjugate complex into the fibrous matrix where it is retained and immobilized;

d) adding a substance capable of producing a signal in the presence of the capture agent analyte/conjugate complex to the fibrous matrix; and e) detecting the signal produced.

Alternatively, steps a) can be performed by simultaneously adding the capture agent, sample and analyte specific conjugate in the shallow incubation well and then washing the mixture into the read well. In another alternative method, step b) can be performed by contacting the analyte/conjugate complex with capture agent in the shallow incubation well to form a microparticle analyte/conjugate complex and then washing this complex into the read well.

In yet another another embodiment step a) can be performed by incubating a sample with the capture agent in the shallow incubation well and then washing the capture agent analyte complex into the read well. Alternatively, step b) can be performed by incubating a capture agent analyte complex with an analyte specific conjugate to form a capture agent analyte/conjugate complex, which is washed into the read wall.

The disposable device can also be employed to conduct competitive assays. A competitive assay comprises incubating a sample and capture agent with a labeled antigen in the shallow incubation well, washing the reaction mixture into the read well and detecting the product formed.

DETAILED DESCRIPTION OF THE INVENTION

The present invention is directed toward a device for performing a solid-phase immunoassay and methods for performing solid phase immunoassays with this device. The device is disposable and is suitable for use with an apparatus having programmed instructions and means for adding sample and reagents, injecting a wash solution to transfer the assay reaction mixture from the incubation well to the read well and for optically reading the results of the assay.

The present invention also provides for a method of transferring reaction mixture from incubation well to read well without physically contacting the reaction mixture with a pipette or other transfer means. Thus contamination of the assay and apparatus is avoided which increases the sensitivity and accuracy of the assay. Sensitivity of the assay is further enhanced by performing incubation and read steps in two separate wells thus decreasing the possibility of non-specific binding of conjugate in the read well and decreasing background signal.

The present invention also provides various methods for performing a solid-phase assay employing the disposable device and the method of transfer and washing of reactants.

The device is designed to be employed in a variety of solid-phase diagnostic assays such as sandwich or competitive binding assays. The device is also designed so that it can be used for fluorescence or colorimetric detection methods. In addition, a special feature is designed into this device to allow light tight seal for chemiluminescence measurements. Further the device of the present invention can be used for microparticle capture or ion capture methods of separating the immunochemical reaction products.

The device is molded to have sets of wells, each set comprises a shallow incubation well for receiving a sample which communicates through a sloping passage means with a read well for detecting the results of the assay procedure. Preferably, the device is molded of opaque polystyrene acrylonitrile-butadiene-styrene terpolymer (ABS), polycarbonate, polyacrylates or some other moldable material which is inert to the assay components.

Samples which can be assayed by the device include biological fluids such as whole blood, spinal fluid, urine, serum and plasma. It is also envisioned that other fluid samples of a non biological nature can be analyzed using the disposable device. The sample is placed either manually or mechanically into the shallow incubation well and reacted (hereinafter described) and after an appropriate time transferred and washed into the read well where the results of the assay are monitored or detected.

Figure 1:
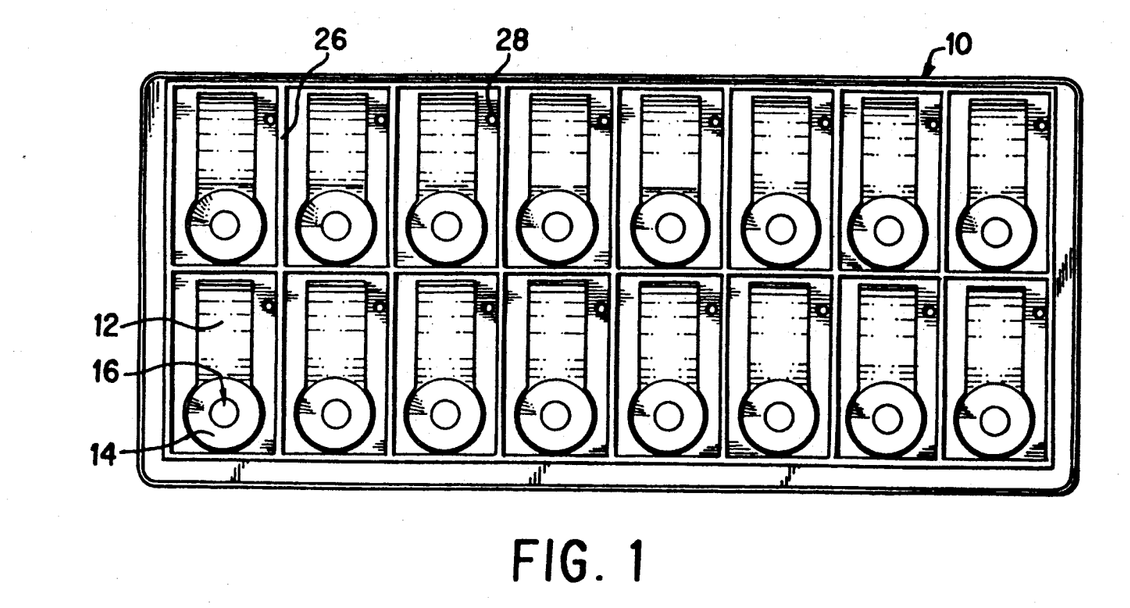
FIG. 1 is a top plane view for one embodiment of the diagnostic device.
Figure 2:
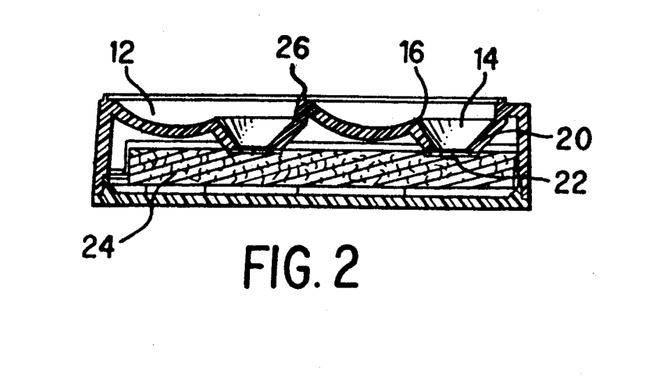
FIG. 2 is a side view and cross section of the diagnostic device 10 of FIG. 1 cut along the short axis.
Figure 3:
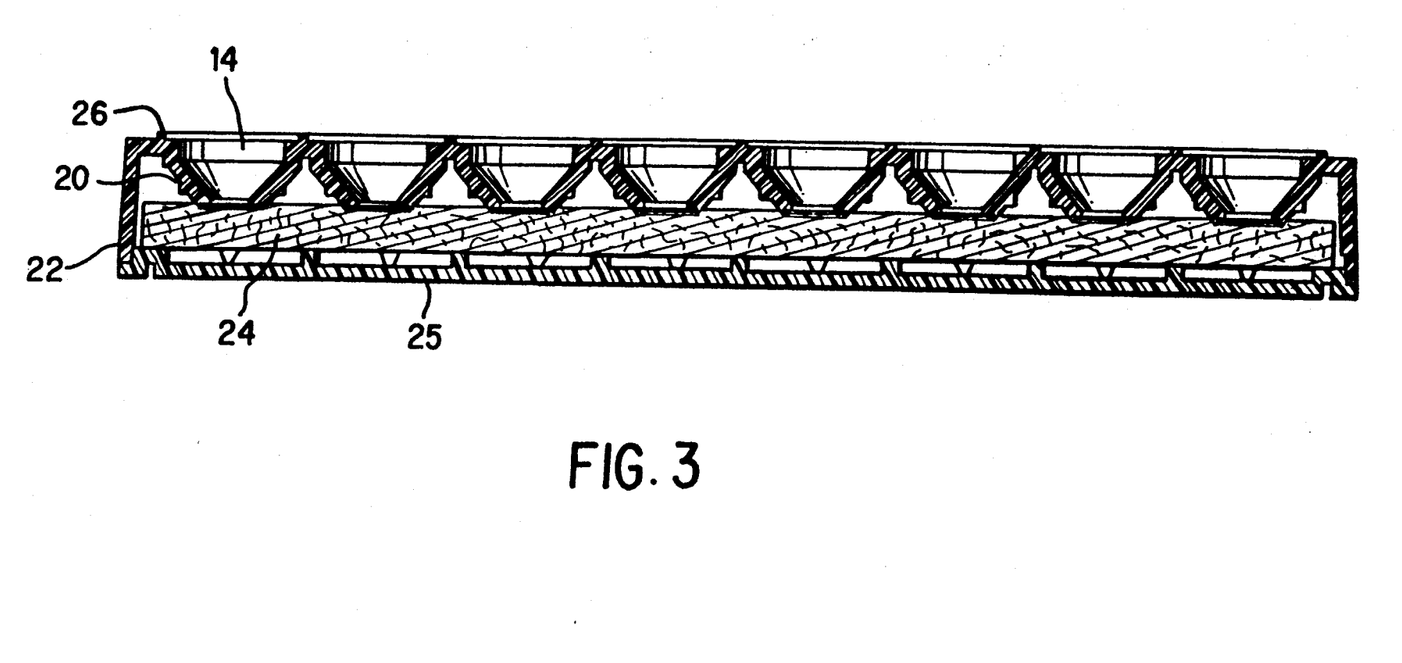
FIG. 3 is a side view and cross section of the diagnostic device 10 of FIG. 1 cut along the long axis.

In one embodiment of the present invention is the device 10 shown in FIGS. 1 and 2, having a plurality of the shallow incubation well 12, passage means 16 corresponding read wells 14 Each read well 14 has a holding means 20, a fibrous material 22 assembled into a square or a rectangular array. Each read well element has a separate porous fibrous matrix 22 and either a separate absorbent material element 24 or a common absorbent material pad, or layers of absorbent material pads. It can also be assembled in such a way that individual absorbent material elements 24 are in intimate contact with the fibrous matrix 22 on one end and with a common absorbent layer on the other end. Any of the absorbant material configurations is chosen to enhance diffusion of fluids away from the porous fibrous matrix 22. The array assembly is preferred where a high throughput instrument is desired. The surface feature 26 is an array of rectangular ribs each rectangle encloses an incubation well/read well pair and acts as a light seal when a chemiluminescence detector, with matching groove padded with compressible polymeric material, mates with it. Vent hole 28 is associated with each incubation well/read well pair. It vents out the air originally entrapped in the absorbent pad and is displaced by reaction mixture and transfer and wash solutions. Intimate contact with the porous matrix 22 and the absorbent material 24 by compressing the absorbent material against the porous matrix using surface features 25 on the internal bottom surface of the disposable device 10.

Shallow incubation well 12 can be semi-spherical, semi-cylindrical, toroidal or any complex curvature with no sharp corners. The largest radius of curvature of the shallow incubation well is along the axis connecting the incubation well to the read well. Dimensions of the shallow incubation well 12 are chosen to maximize the volume of reaction mixture that can be incubated in the well, without having a steep fluid exit angle. A high fluid exit angle requires high wash solution injection speeds. Under these conditions fluids from incubation wells may overshoot the read well as they are transferred. On the other hand low exit angles may lead to self transfer or spilling of reaction mixture into the read well. Choice of dimensions and their relationship to fluid properties can be easily calculated by those skilled in the art.

Figure 4:
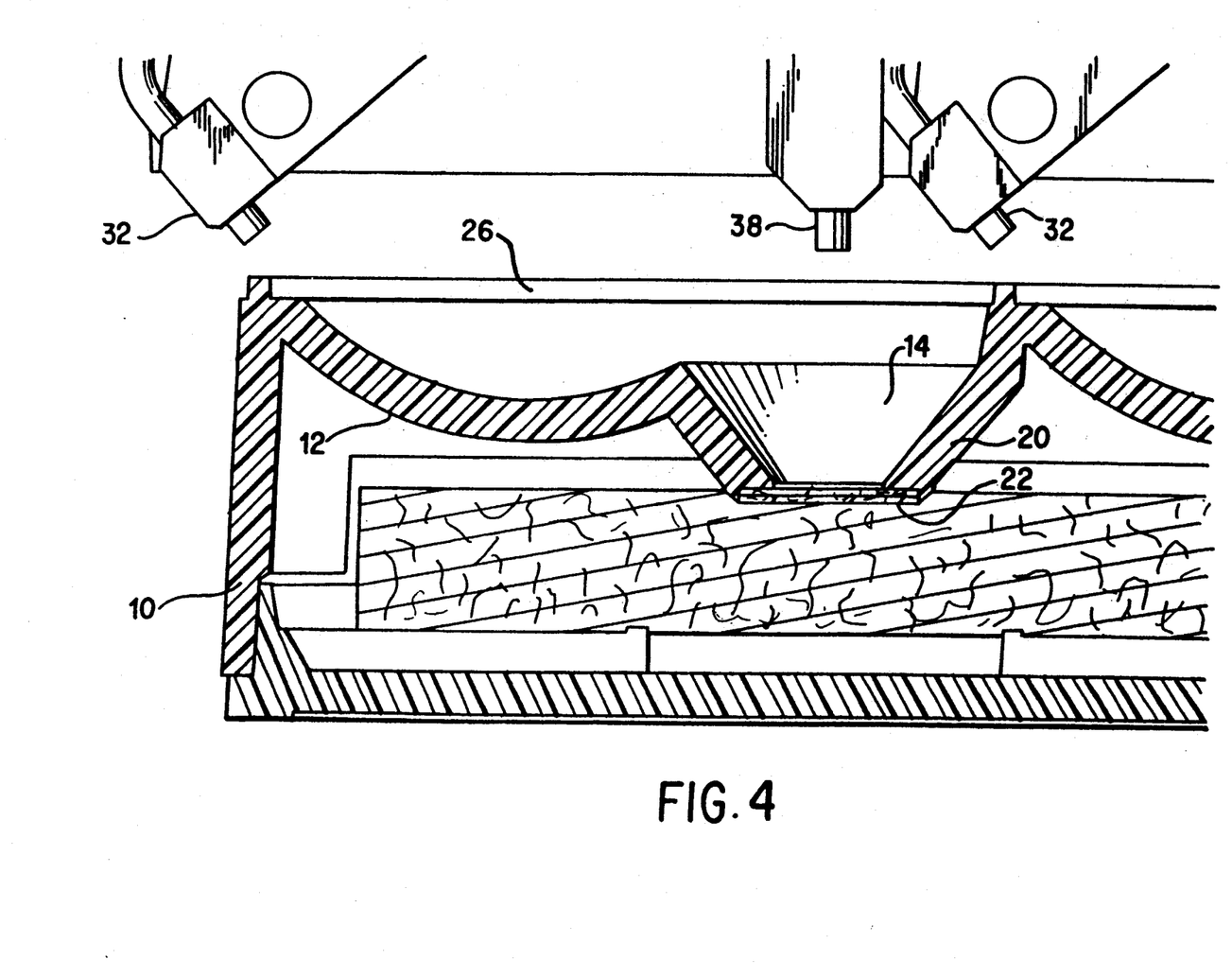
FIG. 4 shows a side view and cross section of a single well pair of diagnostic device 10 positioned for transfer under device 30.
Figure 4A:
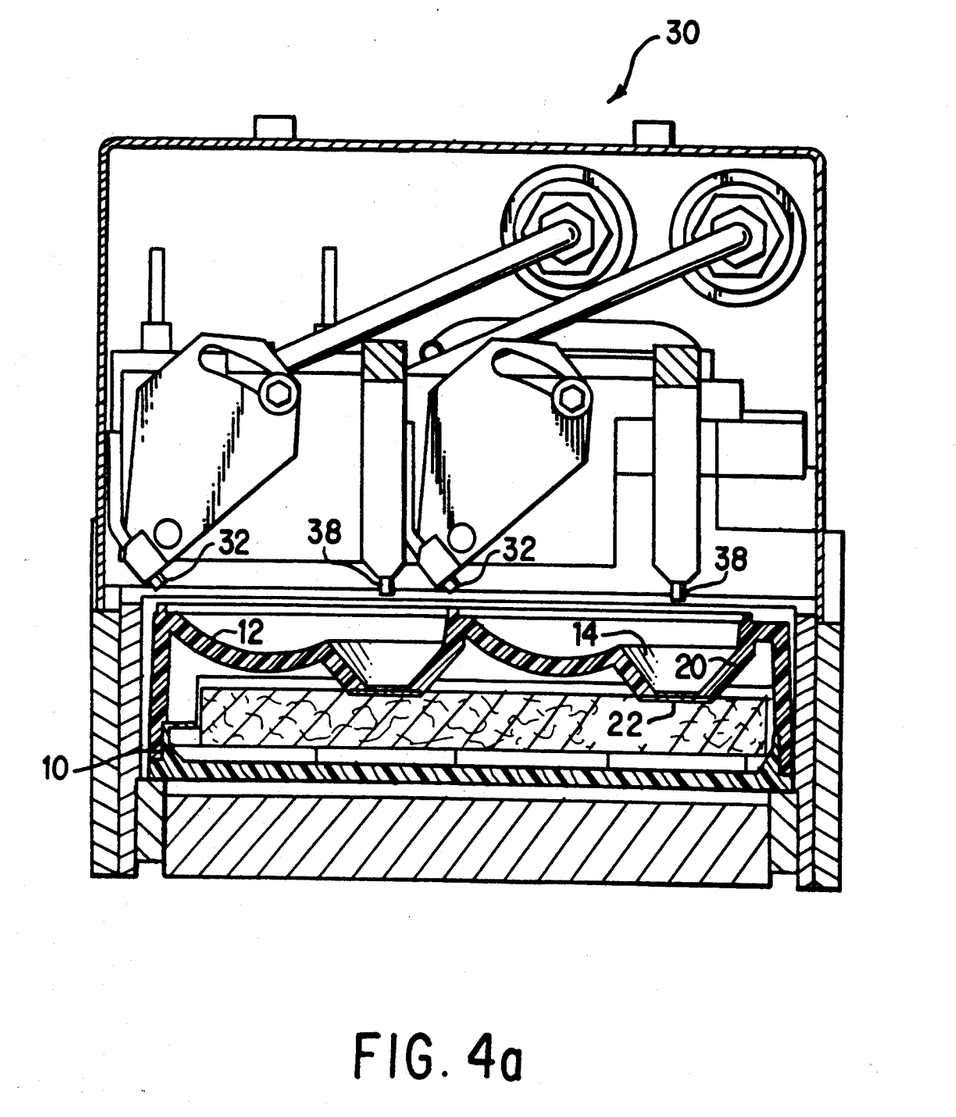
FIG. 4a shows a side view and cross section of diagnostic device 10 positioned for transfer under device 30.

Transfer takes place by injecting wash fluid at the side of the shallow incubation well 12, farthest from the read well 14 using a transfer and wash device 30 shown in FIG. 4. A group of nozzles 32 are positioned close to the surface of the incubation well 12 to inject wash solution. Said solution is injected into the shallow incubation well 12 at a small angle to the tangent to the surface of the well at its region of intersection with the meniscus of the reaction mixture. Angle between direction of wash solution injection and tangent to shallow incubation well surface are generally kept below 45°. Angles between 5° and 20° are preferred.

Wash solution injection volumes and speeds at which it is injected into the shallow incubation well 12 depend on the reaction mixture volume needed to be transferred. Slow wash solution injection speeds into the shallow incubation well 12 may lead to a partial transfer and successive dilution to reaction mixture. Larger wash solution volumes will be required to complete the transfer, which in turn necessitates a larger capacity of absorbent material 24 and hence a larger size disposable. The other extreme of high wash solution injection speeds into the shallow incubation well 12, transferred reaction mixture may overshoot read well 14 and introduces the possibility of reaction mixture or wash solution splashing back towards the injectors and contaminating them. In other words, depth and curvature of shallow incubation well 12, angle of exit port 16 and volume and injection speed of wash solution are dependent on the total assay volume to be incubated in well 12. Total assay volume in turn is optimized to achieve the desired binding reaction under the constraints of assay conditions. Those who are skilled in the art of fluid dynamics can calculate and optimize these dimensions once the essence of this invention is understood.

The read well 14 generally comprises a sloping down entrance port and holding means 20, a porous fibrous matrix 22, and an absorbent material 24. The entrance port and holding means 20 can be a molded portion of the device and preferably a funnel-like structure and is an integral part of the incubation well 14. The holding means 20 is designed with sloping sides which contact the upper surface of the fibrous matrix 22 and is sized to hold a sufficient amount of sample, conjugate material or other reagents to satisfy the requirements of the particular assay being performed. The holding means 20 should be sufficiently opaque or preferably made of black plastic material to decrease background interference with the optics system.

Each pair of incubation wells and associated read well is surrounded by a raised portion, preferably in the form of a rib or a thin plastic wall 26 which is a molded feature of the disposable device and acts as a mating part for another feature on a chemiluminescence reader to create a light tight seal. The height of such light seal is 0.020 to 0.10 inches and preferably 0.04 to 0.08 inches.

Figure 5A:
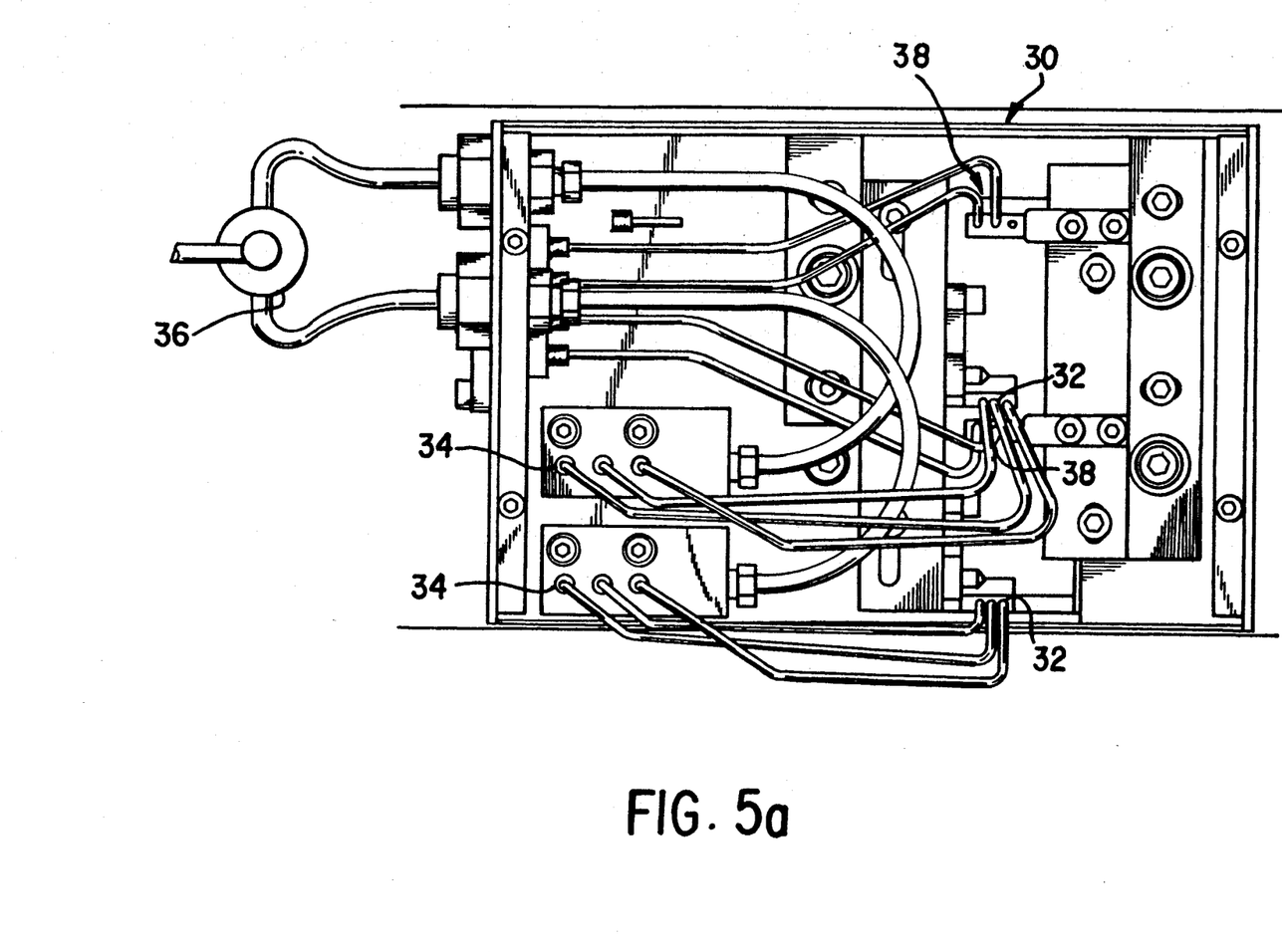
FIG. 5a shows an expanded top vie of device 30.
Figure 5B:
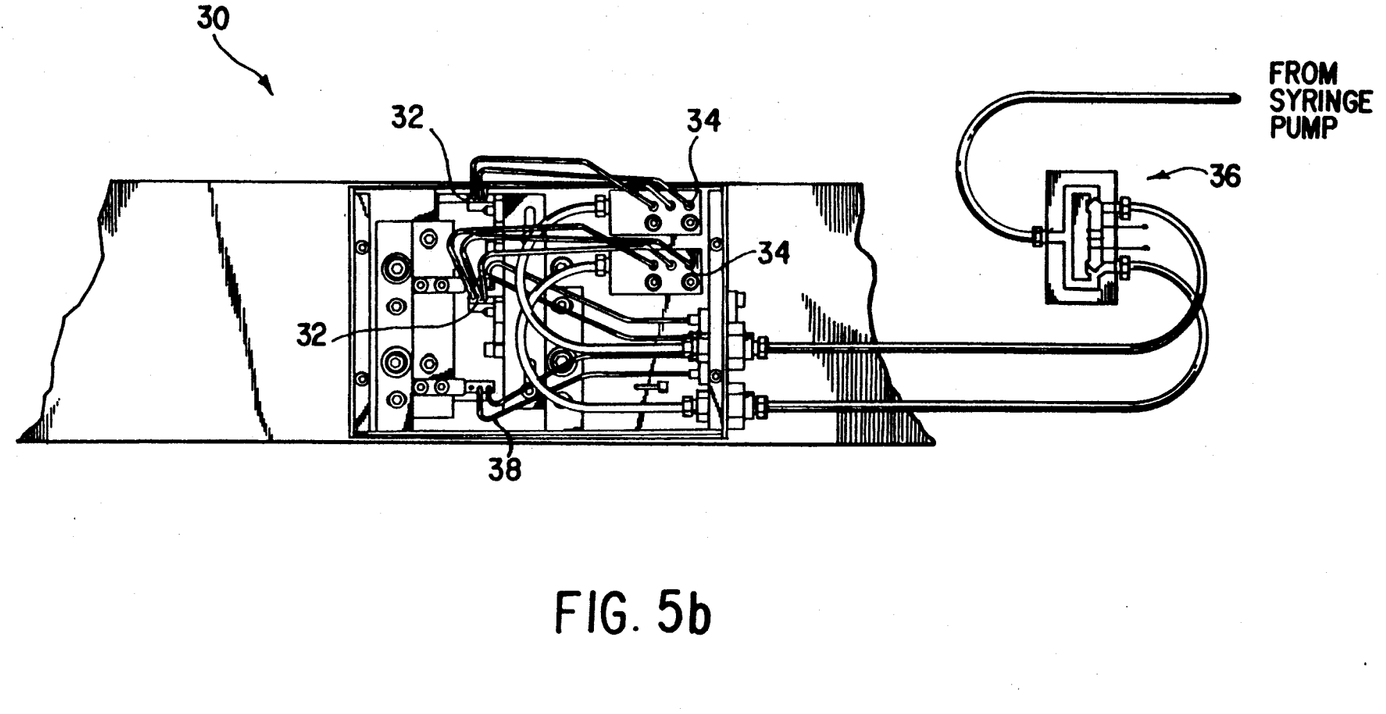
FIG. 5b shows a top view of device 30.

In a preferred embodiment of this invention is the transfer device 30 that is comprised of two sets of nozzles 32. Each set of nozzles is directed towards an incubation well of the reaction tray 10 that has two rows of incubation well/read well pairs. Each set of nozzles is connected to fluid distribution manifold 34 into which wash solution is injected via a stepper motor controlled pump. The first set of nozzles is directed towards the first incubation well of the plurality of well pairs and the second set of nozzles is directed into the second parallel incubation well and fluid flow is diverted to the second set of nozzles via a valve 36 using the same pump. Alternatively an independent pump can be used for each set of nozzles. Thus the transfer process can be performed on two parallel incubation wells either sequentially or simultaneously. A single pulse or several pulses of transfer solution are injected into the incubation well with a delay time between injections to allow the transferred fluids to drain from the read well 14. This prevents splashing and back washing of the reaction mixture from the read well into the incubation well, an action that can reduce transfer efficiency. Drainage time between fluid transfers can be 2 to 180 seconds, preferably 2 to 60 seconds and more preferably 2 to 15 seconds.

In the same transfer device and located on top of the parallel read wells 14 is another set of nozzles 38, each nozzle is connected to a pump either directly or via a valve and can be used to deliver a reagent to the transferred and washed reaction mixture on the fibrous pad 22. Once such nozzle can be used for adding additional wash solution into the read well to transfer any capture agent analyte/conjugate complex on the walls of the retaining means 20 into the fibrous matrix 22 where it is retained and immobilized, this in turn decreases fluctuations in assay numbers due to varied amounts of retained immune complex. The same nozzle can be used to wet the fibrous pad with wash solution before transfer to improve fluid flow into the pad and the absorbent material. Another nozzle can be used for adding a second reagent to the transferred reaction mixture on the pad 22.

The transfer and wash solution preferably contains a small amount of detergent in order to decrease the surface tension and improve wetting the plastic and facilitate transfer. Detergents such as Tween®, sodium dodecyl sulfate or lithium dodecyl sulfate can be used for this purpose. Other surface active agents can be contemplated and used by those skilled in the art.

An alternate way to transfer reaction mixture from shallow incubation well 12 into read well 14 is to use a combination of air and wash solution nozzles. Alternating wash solution nozzles and compressed nozzles in the group of nozzles directed towards the wall of the shallow incubation well 12 and simultaneously activating them can affect the same transfer described previously. This saves in the fluid volume used in the assay and hence in the volume of fluids to be disposed of in the absorbent material 24.

Figure 6:
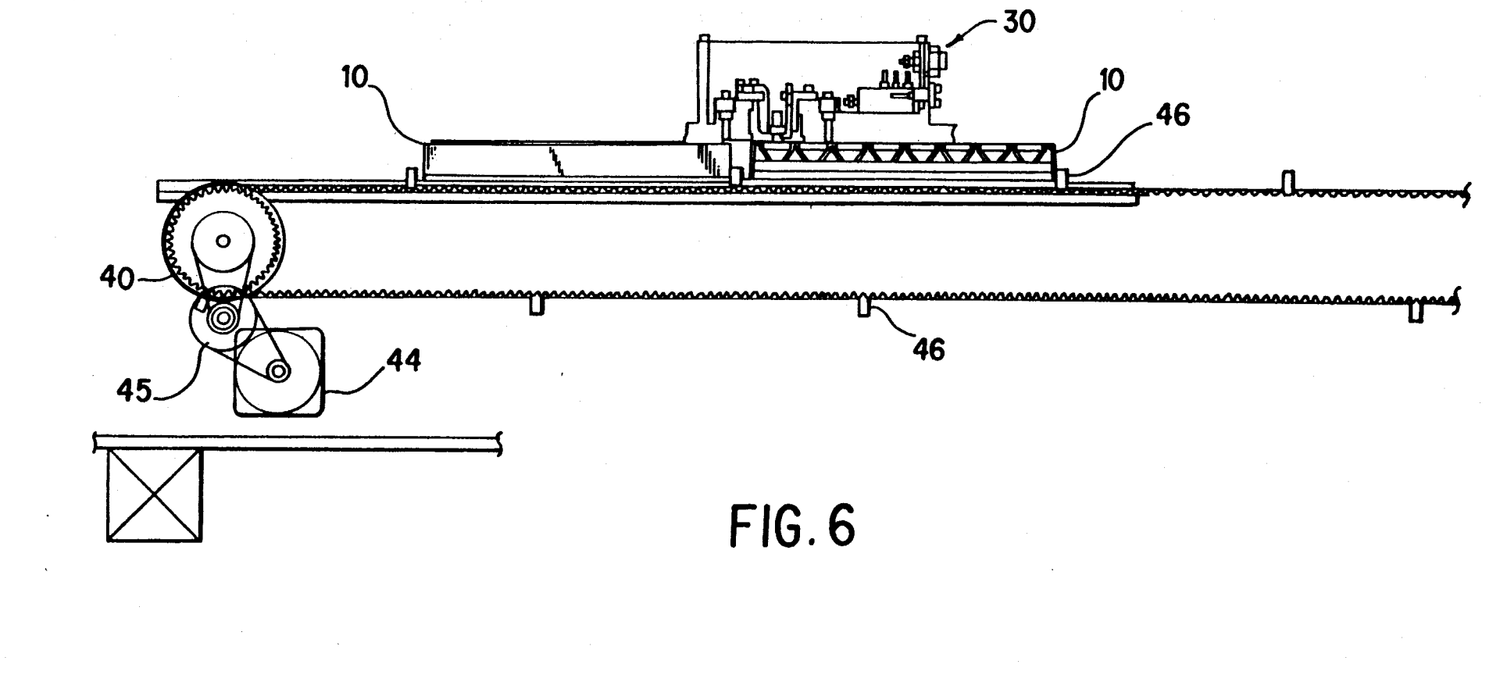
FIG. 6 shows the transport mechanism for moving device 10 under the transfer device 30.

The transfer device 30 can be moved by robotic means and accurately positioned on subsequent incubation wells to affect transfer and wash of the reaction mixture. A preferred way to bring new wells under the transfer device 30 is to move the disposable device 10 in a controlled manner under the transfer device 30 using a mechanism 40, comprised of a timing belt 42 controlled by a stepper motor 44 and gear reduction system 45. A rectangular plastic log 46 pushes the disposable device 10 to new positions. Other means of moving the disposable device such as the use of linear actuators, metal belts or screw drives can be contemplated and used by those skilled in the art.

The porous fibrous matrix 22 is a thin disk-like material positioned below the entrance port and holding means 20 to retain and immobilize a complex from which an assay signal can be read. The phrase "retain and immobilize" means that the captured/labeled immune complexes while upon the fibres of the material are not capable of substantial movement to positions elsewhere within the material, (i.e., to other fibers), and cannot be removed completely from the material without destroying the material.

The pore size or spatial separation of the fibers comprising the fibrous matrix 22 is essential to the overall performance of the solid-phase immunoassay contemplated by the present invention. It must allow adequate void areas to assure the proper flow of reagents and sample through the fibrous matrix. Specifically, the spatial separation of the fibers must be larger than the diameter of the microparticles employed in a microparticle capture assay in such a way that after the microparticles are deposited on the fibrous matrix, the matrix is not blocked but instead remains porous. As used herein "porous" means that the matrix is and remains a material into which fluids can flow and can easily pass through without the need to apply vacuum or pressure to facilitate its flow.

The fibrous material of the present invention can be chosen from any of a variety of materials such as glass, cellulose, nylon or other natural or synthetic fibrous material well known to those skilled in the art. A suitable material is H&V Product No. HC411 glass fiber filter paper, which has a nominal thickness of 0.055 inches and is commercially available from Hollingsworth and Vose Co., East Walpole, Mass. The thickness of such material is not critical, and is a matter of choice for one skilled in the art, largely based upon the properties of the sample being assayed, such as fluidity.

The fibrous matrix 22 is positioned against the holding means 20 and above a means that functions to facilitate the transportation of fluid through the fibrous matrix. This can be a reservoir means to which reduced pressure is applied during or after the transfer, or an absorbent element made of any moisture or fluid-retaining material which effectively retains fluid passing through the fibrous matrix 22. A preferred embodiment of this invention is that an absorbent material 24 is positioned below the fibrous matrix 22 and is in intimate contact with the lower surface of porous matrix 22 in order to absorb any reagent that flows through the fibrous matrix. This contact assures rapid transportation of the reaction fluids through the fibrous matrix 22.

The microparticles employed to perform the solid-phase immunoassay are selected to an average size that is preferably small enough such that they are suspendable in water or a sucrose solution to facilitate their coating with an antibody or antigen. The average individual size of the microparticles which can meet both of the above requirements is from about 0.1 to about 50 microns, more preferably from about 1 to about 10 microns in diameter. The microparticles can be selected from any suitable type of particulate material such as polystyrene, polymethylacrylate, polypropylene, latex, polytetrafluoroethylene, polyacrylonitrile, polycarbonate or similar materials.

Uncoated microparticles can be employed for binding some analytes but in many situations the particles are coated with a substance for binding an analyte, e.g., antibody or antigen, or a combination thereof.

The transfer and treatment of a sample with reagents in the device is preferably but not necessarily accomplished by automated means under computer control. Robotic arms can supply the necessary reagents by various transferring means communicating with reagent containers located external to the device and associated mechanisms. Most importantly instrument mechanism or robotic means can position a pipetting or jet means for directing a stream of wash solution into the shallow incubation well 12.

Alternatively the assay device 10 can be placed on a conveyor where a timing belt can move it at precise time intervals to locations under automated pipettors, reagent dispensers transfer devices, washing devices or detectors. Whether a linear or circular motion is used to move the disposable, it is ultimately brought under a transfer device which successively injects transfer fluid into well 12 to wash the assay reaction mixture through passage means 16, into the read well 14. This particular feature of the device 10 prevents contamination of the automated apparatus or pipetting means as well as the assay reaction mixture. Also, because a pipette never needs to be washed to prevent cross contamination of other assays.

For illustration purposes the following procedures are provided:

In one form of a sandwich assay method a sample is added to the shallow incubation well and the device is placed on a transport means designed to hold a plurality of devices. Steps (a) through (e) may be performed by a microprocessor-controlled automated instrument or manually as follows:

(a) an analyte-specific conjugate is added to the shallow well containing a sample to form a mixture which is incubated for a sufficient time to allow any analyte present to complex with the analyte specific conjugate;

(b) microparticles are added to the mixture to form a microparticles analyte/conjugate complex; alternatively, the analyte/conjugate complex can be washed into the read well to which microparticles have been previously or simultaneously added;

(c) the incubated microparticles analyte/conjugate complex is washed into the receiving port of the read well and washed with a suitable buffer or water to transport the complex into the porous fibrous matrix;

(d) an indicator substance capable of producing a color change or other detectable signal in the presence of the microparticle analyte/conjugate complex is added to the read well; and (e) the assay signal is detected by optical means as a function of the presence or amount of analyte in the sample.

In a variation on the above procedure, steps (a) and (b), i.e., formation of analyte/conjugate complex and formation of microparticle analayte/conjugate complex, respectively, can be performed simultaneously by adding the capture agent, sample and analyte-specific conjugate to the shallow incubation well and incubated. The complex is then washed into the read well.

In the final step (e), detection of the signal produced in the read well varies with the type of label used. Thus for an enzyme labeled antigens or antibodies, a substrate solution is added in the read well and the product formed is detected by color development or generation of a fluorescent signal. For fluorophore labeled antigen or antibodies, direct excitation of fluorophore and detection of spontaneous or time resolved fluorescence signal is used. In the case of chemiluminescent labeled antigens or antibodies, detection is achieved by chemically activating the luminescent label and monitoring generated light. In all these methods of detection, either the total integrated signal over a period of time or the rate of change of signal over the observation period can be used to establish a standard curve for the assay and determine the concentration of analyte in unknown samples.

In another version of a solid-phase sandwich assay procedure the automated or manual steps can be performed as follows:

(a) a sample and capture agent are mixed together in the incubation well to form a complex of the microparticle and analyte;

(b) the microparticle analyte complex is treated with an analyte specific conjugate and incubated to form a microparticle analyte/conjugate complex (alternatively steps (a) and (b) can be performed simultaneously by adding sample, capture agent and an analyte specific conjugate to the incubation well, incubating and washing the complex formed into the read well);

(c) the complex is then then transported into the fibrous matrix by applying a wash of a suitable buffer or water through injector means;

(d) an indicator substance capable of producing a signal in the presence of the microparticle analyte/conjugate complex is added to the read well to form an assay signal;

(e) the assay signal is detected by optical means as a function of the presence or amount of analyte in the sample.

In yet another solid-phase immunoassay approach the disposable device can be employed to perform a competitive binding assay. The automated or manual steps are as follows:

(a) a sample is added to a known amount of labeled antigen and capture agent capable of binding a suspect antigen to form a mixture in a incubation well;

(b) the mixture is washed into the read well where the capture agent become bound to the fibrous matrix;

(c) the fibrous matrix is washed to remove unbound antigen;

(d) an indicator substance is added to the read well to form an assay signal in the presence of the labeled antigen; and (e) the assay signal is detected by optical means as a function of the presence or amount of analyte in the sample.

It should be apparent that many variations of the above steps can be designed to form the microparticles analyte/conjugate, complex which can be detected by optical means on the porous fibrous matrix. Generally the sandwich or competitive assay procedure and the choice of an analyte specific conjugate, and indicator substance are known to those skilled in the art and therefor are not discussed in great detail here. Instead, the present invention is directed toward the device described above and the method of transfer, and in a preferred embodiment to the device which is suitable for the automated performance of a solid-phase immunoassay process on a microprocessor-controlled automated instrument.

This method of incubation in one component, fluid transfer, separation and signal generation in another compartment described in this invention is not limited to microparticle based immunoassays. Thus another preferred embodiment of the invention is to use an ion capture separation method as described above. The different procedures and examples described above for the use of microparticles as a capture phase can be used with ion capture, whereas a polyanionic material attached to a hapten, antigen or antibody is used as a capture agent in-place of the microparticles in each example. After transfer of the polyanionic material to the positively charged glass fiber pad, the immune complex is retained and immobilized on the glass fiber pad by ionic forces.

Competitive binding ion capture immunoassay can be performed according to the method of the present invention. In this method the fibrous pad 22 is treated with a material that causes the surface to be positively charged, like water soluble polymeric materials with quaternary ammonium groups. Commercially available Celquat ™ L-200 (from National Starch and Chemical Company, Bridgewater, N.J.) can be used for this purpose. The sample is incubated in the shallow incubation well with a labeled anti body for the analyte, a capture phrase is then added which is composed of the analyte molecule chemically bound to a an anionic polymer such as polyglutamic acid. After a second incubation the reaction mixture is transferred to the fibrous pad using injected transfer and wash solution.

EXAMPLE I

A disposable reaction tray was constructed according to the embodiments of this invention from two injection molded parts. The disposable tray was 6.800 inches long, 3.125 inches wide, and 0.800 inches high. The top part incorporated a two by eight rectangular array of the shallow incubation wells. Associated with each well is the funnel-like structure and the passage way between them described in the invention. The capacity of the incubation well is 280 micro liters and the capacity of the funnel is 480 micro liters. The center to center spacing of the two adjacent incubation wells or two adjacent funnels is 1.4173 inches (36 mm). The pitch of the rows of consecutive wells was 0.800 inches. The funnel-like structure has a cutting edge on the inside surface. The height of the surface feature for light sealing is 0.040 inches and its width is 0.040 inches. The vent hole was located 0.250 inches from the edge of the light baffle and was 0.060 inches in diameter. The top part was injection molded of black ABS. The bottom part was an injection molded piece of white ABS which mates with the top part and can be sonically welded to it. The top and bottom parts have surface features to fix a slab of absorbant material in place. The top part of the disposable device was turned upside down and a sheet of fibrous glass was placed inside the disposable, covering the bottom part of the read wells. The fibrous material was pressed against the cutting edges on the bottom of the funnel-like structures to cut individual filter pads for each well. The over-all diameter of each pad was 0.350 inches. The active area, facing the detector, was 0.210 inches in diameter. After the fiber pad was press-cut, the rest of the sheet was removed. This method of cutting the fibrous matrix, removing the excess material, and having an individual fibrous pad for each well is preferred as its prevents seepage of fluids between two adjacent wells and improves assay sensitivity. The absorbant material was placed in the top part of the disposable in contact with the glass fiber pads. It is a rectangular slab 6.5 inches long, 3 inches wide and 0.265 inches thick. The material was cellulose acetate manufactured by the American Filterona Company, Richmond, Va. The absorbant pad was pressed against the glass fiber disks by the bottom part. The surface features on the bottom part is in the form of a group of rings, each is concentric with the funnel-like structure and has a diameter of 0.665 inches and its rib is 0.120 inches high. The preferred design ring pushes the pad of absorbant material against the glass fibrous pad and assures intimate contact between the two pads. The two parts were assembled and welded using a Branson ultrasonic welder, Banson Ultrasonics, Danberry, Conn., with one horn optimized to fit the disposable device.

A transfer and wash device similar to that described in the embodiments of this invention was constructed. Sample and reagents were incubated in the shallow incubation well. Wash solution was injected from an assembly of three adjacent nozzles 0.5 mm nominal diameter made of Teflon ® tubing and connected to a machined polyacrylic manifold by minstac fittings from the Lee Company, Westbrook, Conn. The manifold was connected through a seloniod activated three way valve (Angar Scientific, Florham Park, N.J.) to a stepper motor controlled syringe pump. Nozzles were directed at an angle of 13° to the tangent to the shallow well surface at its point of intersection with reaction mixture surface. In this geometry nozzles were at a 60° angle to the horizontal plane. Wash solution was injected in the manifold at the rate of 1250 µL per second. The average linear injection speed was 2.1 m/second. The exit angle of fluid was 28°. Two aliquots 300 µL each of wash solution were injected into the incubation well to affect transfer. A delay time of 10 seconds was allowed between the two injections to allow for the fluids to drain through the pads. The capacity of the funnel was sufficient to prevent wash back. Transfer solutions preferably contained an amount of detergent such as 0.0250–0.1% Tween ®, 0.025–0.1% sodium lauryl sulfate or lithium lauryl sulfate to prevent beading of fluids in the incubation well and facilitate fluid transfer.

Three additional nozzles or were installed in the transfer device and centered on the pad. They were used either in groups or independently to wash the reaction mixture off the walls of the funnel into the pad or to deliver conjugate solution to the pad.

EXAMPLE II

The method of transfer and the function of the transfer device was tested by determining the efficiency of transfer of labeled chemiluminescent microparticles from the incubation well to the read well of the disposable device of example 1, using the following method:

Acridinium sulfonamide labeled antibody or Hepatites B core antigen, pooled from lots prepared for clinical trials, concentration 5 μg/mL, was diluted in conjugate diluent, containing 50% fetal calf serum (Abbott Laboratories manufacturing stock), 2% human plasma, 0.1% Tween ®-20, 0.1% ethylenediamine tetra acetic acid and 0.1% sodium azide in phosphate buffered saline, pH 6.8. The final conjugate concentration was 150 ng/mL. Carboxylated polystyrene microparticles coupled to antibody to Hepatites B core antigen as an undercoat and then with recombinant Hepatites B core antigen were pooled from lots prepared for clinical trials and contained 0.3% solids by weight. Microparticles were suspended in phosphate buffered saline (Abbott Laboratories, North Chicago, Ill.), pH 7.2, containing 16% sucrose. A 0.1% solution of Tween ®-20 in phosphate buffered saline, pH 7.2, was used as a transfer solution.

Luminescent microparticles for the determination of transfer efficiency were prepared by mixing 50 ml of conjugate solution and 50 ml of microparticles suspension. The reaction mixture was incubated in a wash bath at 40° C. for two hours. It was then let stand at room temperature for 24 hours to ensure complete binding of acridinium sulfonamide labeled antibodies to the antigen labeled microparticles.

100 μL of luminescent microparticles and 100 μL fetal calf serum were dispensed in each of the 16 shallow reaction wells of a disposable described in example 1. The disposable reaction tray was placed on a linear track and moved to a position where it was located under the transfer device of the present invention. The mixture was transferred from the shallow incubation well to the read well using two, 300 μL pulses of transfer and wash solution of a 0.1% Tween ®-20 solution were injected at a linear speed of 2.1 m/second from three nozzles into the reaction well to transfer and wash the serum and microparticles onto the fiber glass pad. The disposable tray was linearly moved to a subsequent position where a chemiluminescence read head where each side of the disposable reaction tray was detected by an independent photomultiplier tube.0 The transfer and washed microparticles on the pad were triggered using 0.3% alkaline peroxide solution. The measured signal for each well was considered to correspond to the amount of the reaction mixture transferred from the reaction well to the read well by the method of the present invention. The mean and standard deviation for each eight wells on each side of the disposable were calculated.

A base line was determined by dispensing 100 μL of luminescent microparticles on the fiber glass pad in each of the 16 read wells of a disposable reaction tray of example I and were allowed to drain through. 100 μL of fetal calf serum and 100 μL of de-ionized water were dispensed in each of the shallow reaction wells of the same disposable. The disposable reaction tray was placed on a linear track and moved to a position where it was located under a transfer device of the present invention. Two aliquots 300 μL each of a 0.1% Tween ®-20 solution were injected at a linear speed of 2.1 m/second from three nozzles into the reaction well to transfer the serum and water mixture in order to wash the microparticles placed on the fiber glass pad with the same volume of fluids used in the first part of the experiment to transfer the microparticles serum mixture, and the disposable tray was moved on the same track by the same mechanism to the reader position under a read head. The washed microparticles on the pad were activated using alkaline peroxide solution and the resulting chemiluminescence signal was integrated for a period of six seconds. The mean and standard deviation of the signals generated in all eight wells in a sub-channel were calculated. The mean value of signal counts for the particles, manually pipetted on the pad corresponds to a 100% transfer.

The efficiency of transfer was calculated by dividing the magnitude of the mean signal generated from the transferred microparticles each side by the signal representing 100% transfer on a corresponding side.

Precision of transfer of the reaction mixture from the reaction well to the read well was determined by repeating each of the two previously described transfer and base-line experiments on three disposable trays. The mean percent transfer and the %CV of the percent transfer were calculated for each side of the three trays. The experiments were repeated for six independent transfer devices mounted on six incubation tunnel and each incubation tunnel was equipped with a read head and associated electronics were controlled by an 310 development system (Intel corporation, Sunnyvale, Calif.)

Results from these studies are shown in table 1. In all instances the transfer efficiency was higher than 95% and the %CV of transfer was well below 5%. The reproducibility of the percent transfer figures indicate the validity of the fluid transfer method of the present invention.

TABLE 1

Efficiency and precision of transfer of immune complex-coated latex particles

| Unit # | Side A % Transfer | % CV | Side B % Transfer | % CV |
|---|---|---|---|---|
| 1 | 98.8 | 0.6 | 96.0 | 1.8 |
| 2 | 96.7 | 1.9 | 96.6 | 2.2 |
| 3 | 101.3 | 1.49 | 98.0 | 1.16 |
| 4 | 96.23 | 3.23 | 97.3 | 0.99 |
| 5 | 98.4 | 3.4 | 100.6 | 2.0 |
| 6 | 98.0 | 1.9 | 99.2 | 1.8 |

EXAMPLE III

Microparticle-Capture Competitive Binding Assay for Hepatitis B Anticore Antibody

Materials

Acridinium sulfonamide labeled antibody to Hepatites B core antigen, pooled from lots prepared for clinical trials, concentration 5 μg/mL, was diluted in conjugate diluent, containing 50% fetal calf serum (Abbott Laboratories manufacturing stock), 2% human plasma, 0.1% Tween ®-20, 0.1% ethylenediamine tetra acetic acid and 0.1% sodium azide in phosphate buffered saline, pH 6.8. The final conjugate concentration was 150 ng/mL. Carboxylated polystyrene microparticles coupled to antibody to Hepatites B core antigen as an undercoat and then with recombinant Hepatites B core antigen, were pooled from lots prepared for clinical trials and contained 0.3% solids by weight. Microparticles were suspended in phosphate buffered saline (Abbott Laboratories manufacturing stock), pH 7.2, containing 16% sucrose. A 0.1% solution of Tween ®-20 in phosphate buffered saline, pH 7.2, was used as a transfer solution.

Samples were anti-core negative control and anti-core positive control from a commercial enzyme immunoassay kit Core panel control that has 50-60% inhibition as measured by a commercial enzyme immunoassay procedure (Corezyme, Abbott Laboratories, North Chicago, Ill.) Two procedures were followed:

read position where a chemiluminescence read head was lowered to mate with the walls surrounding the first two wells on the disposable to create a light-tight seal. The transferred and washed microparticles on the fibrous pad were activated using 0.3% alkaline peroxide solution. The measured signal for each well was considered to correspond to the amount of acridinium labeled conjugate attached to the microparticles. The end point was determined by calculating the percent inhibition of signal wherein % Inhibition=100 (Mean of Negative Control−Mean of Sample)/(Mean of Negative Control−Mean of Positive Control). A % inhibition of 50% and higher was taken as positive and a % inhibition less than 50% was assigned as negative.

Data are tabulated in Table 1. Reproducibility of the percent inhibition figures indicate the validity of the fluid transfer method. Agreement with the standard enzyme immunoassay method shows that a heterogeneous immunoassay can be performed using the method and device of the present invention.

TABLE 2

A One-Step Microparticle Capture Competitive Binding Hepatites B Anticore Antibody Assay

| Sample | Side A | | | | Side B | | | |
|---|---|---|---|---|---|---|---|---|
| | Mean Counts | SD | % I | SD | Mean Counts | SD | % I | SD |
| Negative Control (n = 71) | 37833 | 1028 | −1.5 | 3.0 | 35039 | 772 | −0.26 | 2.4 |
| Positive Control (n = 7) | 2657 | 122 | 100.8 | 0.35 | n = 69) 2174 | 109 | 100.7 | 0.34 |
| Panel (n = 7) | 19106 | 884 | 52.8 | 2.58 | 17126 | 462 | 54.73 | 1.41 |

Data from instrument #2 validation, Lab notebook #35601 pages 89-99

Procedure A

Automated One Step Assay

100 μL of control or sample were pipetted into the shallow reaction wells of a disposable device using an automated pipettor. 50 μL acridinium labeled anti core antibodies and 50 μL of antigen coated latex particles were dispensed into each incubation well. The reaction mixture was incubated for 40 minutes in a heated tunnel at 40° C. with the disposable device moving into the tunnel by a timing belt at steps of 0.80 inches per second per step. It remains in position for 72 seconds for performing an assay step, then it steps again for one step at 0.80 inches per second.

The reaction mixture was transferred and washed from shallow incubation well onto the porous fibrous matrix of read well as the disposable reached under the transfer device. Transfer was affected by injecting two pulses 300 μL each of 0.1% solution of Tween ®-20 into the well from three nozzles in the transfer device. Each nozzle has a nominal diameter of 0.5 mm and the fluid was injected at an average linear speed of 2.1 m/second. A delay time of 12 seconds was allowed between the to pulses to assure drainage of the transferred solution through the pad The transferred microparticles, retained on the pad in the read well, were subsequently washed with three aliquots, 100 μl each, of wash solution. The disposable was moved on the timing belt to allow subsequent well pairs to be located under the transfer device and to transfer the reaction mixture and wash the microparticles retained and entrapped on the fibrous pad. The disposable device 10 was moved at the same rate to a Procedure B Automated Two Step Assay 100 μL of control or sample were pipetted into the shallow reaction wells of a disposable device 50 μL 50 mM cysteine in a diluent containing 10 mM EDTA and 0.01% gentamicin, and 50 μL of antigen coated latex particles were dispensed into each incubation well. The reaction mixture was incubated for 20 minutes in a heated tunnel at 40° C. with the disposable device moving into the tunnel using the same mechanism described for the one step procedure. As the disposable reached under the transfer device the reaction mixture was transferred and washed from shallow incubation well onto the porous fibrous matrix of read well as described in the previous example. A 12 seconds delay was allowed for the transfer and wash solution to drain down the absorbant pad. 50 μL acridinium labeled anti HBc antibodies were dispensed on each fibrous pad from one of the nozzles located in the transfer device and directed on the center of the read well. The disposable was moved on the timing belt to allow subsequent well pairs to be located under the transfer device and to affect transfer of the reaction mixture. The disposable device was incubated for 20 more minutes in the tunnel using the same moving timing belt as it is moved to a washing position.

The transferred microparticles, retained on the pad in the read well, and the excess acridinium labeled antibodies were subsequently washed with three 100 μl aliquots, of wash solution. The disposable device was moved at the same rate to a read position, the transferred and washed microparticles on the pad were triggered using 0.3% alkaline peroxide solution and the chemiluminescence signal was integrated for six seconds. The measured signal for each well was considered to correspond to the amount of acridinium labeled conjugate attached to the microparticles.

A percent inhibition of 50% and higher was taken as positive and a percent inhibition less than 50% was assigned as negative. The cut-off value was set from performing the assay on negative population (200 samples that were confirmed negative for the antibody to Hepatites B core antigen using an enzyme linked immunosorbent assay ELISA procedure.

TABLE 3

A One-Step Microparticle Capture Competitive Binding Hepatites B Anticore Antibody Assay

| Sample | Side A | | | | Side B | | | |
|---|---|---|---|---|---|---|---|---|
| | Mean Counts | SD | % I | SD | Mean Counts | SD | % I | SD |
| Negative Control (n = 70) | 31610 | 1066 | 0.4 | 3.8 | 26839 | 583 | −1.3 | 2.5 |
| Positive Control (n = 7) | 3399 | 391 | 101.7 | 1.4 | 3260 | 474 | 100.3 | 2.0 |
| Panel (n = 7) | 15452 | 988 | 58.4 | 3.5 | 14102 | 355 | 53.6 | 1.5 |

EXAMPLE IV

Ion-Capture Based Competitive Binding Hapten CLIA

This example shows the use of the device and method of this invention in a competitive binding assay for the abused drug phenylcyclidine (PCP) in urine employing ion capture immunoassay procedures described above. The formation of the immune complex in the shallow reaction well of the disposable device of this invention involves the use of an anionic polymer as a capture agent. The reaction mixture is transferred to the read well of said device and and tan immunochemical reaction product is immobilized by ionic forces on the fibrous pad of said device that has been previously treated with a solution of a cationic polymer.

Anti-phenylclidine antibodies were labeled with acridinium sulfonamide using EDAC coupling procedures. Prewet and transfer solutions were IMx buffer (Abbott Laboratories, North Chicago, Ill.) containing 25 mM Tris,). 0.3M sodium chloride, 0.1% sodium azide, pH 7.2. The cationic polymer was a 0.5% aqueous solution of Celquat TM L-200 (National Starch and Chemical Company; Bridgewater, N.J.) in 10 mM sodium chloride.

The capture agent phenylcyclidine-polyglutamic acid was prepared according to the following steps:

1 gm of polyglutamic acid sodium salt (Sigma Chemical Company, Saint Louis, Mo.) were added to 7 gms of AG50W-X8 ion exchange resin (from Bio-Rad, Richmond, Calif.) in 20 mL water and stirred overnight. Liquor was removed and lyophilized to give free acid polyglutamic acid (PGAFA).

Phenylcyclidine-4-chloroformate was prepared by reacting 1.4 mg 4-hydroxyphenylcyclidine (4.24 $10^{-6}$ moles) in 0.5 mL tetrahydrofuran with 0.5 ml of 10% solution of phosgene in benzene (130 mole excess). The reaction was allowed to proceed for 2.5 hours at room temperature. Solvent was evaporated under a stream of nitrogen to yield a residue of phenylcyclidine-4-chloroformate. The residue was dissolved in 0.5 mL tetrahydrofuran and 1.7 mg of free acid poly-glutamic acid (molecular weight 40,000) in 0.5 mL 1-methyl-2-pyrolidine was added to it. The reaction was carried out overnight at room temperature then the reaction mixture was evaporated to dryness. The dried mixture was dissolved in 1.5 mL phosphate buffer, pH 7.0 and dialyzed against 0.1M sodium phosphate at ph 7.0 in a 30,00 molecular weight cut-off dialysis bag. The precipitate was filtered and dissolved in phosphate buffer. The cloudy aqueous filtrate was extracted with methylene chloride till it was clear. The aqueous layer was diluted in a buffer containing 1% fish gelatin, 25 mM Tris, 100 mM sodium chloride, 1 mm magnesium chloride, 0.1 mM zinc chloride and 0.1% sodium azide at pH 7.2 to yield 5 $\mu$gm/L phenylcyclidine-PGA capture reagent. Trigger solution: 0.3% alkaline peroxide solution in 0.25M sodium hydroxide.

Samples were phenylcyclidine calibrators from a TDx TM fluorescence polarization immunoassay kit (Abbot Laboratories, North Chicago, Ill.). They contained 500, 250, 120, 60, 25, and 0 ng/mL phenylcyclidine in human urine.

Procedure

50 $\mu$L of prewet solution followed by 50 $\mu$L Quat solution were dispensed on the fibrous glass pad of disposable reaction tray of the present invention.

50 $\mu$L of control or sample were pipetted into the shallow reaction wells of a disposable device of this invention using an automated pipettor. 50 $\mu$L of acridinium labeled anti-PCP antibodies were dispensed into each incubation well. The mixture was incubated for 9.8 minutes in a heated tunnel at 32° C. with the disposable device moving into the tunnel by a timing belt in steps at the rate of 0.8 inches per minute. The device would stay stationary for 36 seconds after each step for a reaction step to take place. After 9.8 minutes incubation on the moving timing belt 50 $\mu$L a solution containing PCP-PGA capture reagent was dispensed into the incubation well. The reaction mixture is further incubated for 9.8 minutes. The quaternary ammonium-polymer treated pad was rinsed with 100 $\mu$L of the IMx buffer before reaction mixture transfer. As the disposable reached under the transfer station the reaction mixture was transferred and washed from shallow incubation well onto the pre-treated porous fibrous in the read well. Transfer was affected by injecting a single pulse of 350 $\mu$L of IMx buffer into the well at a speed of 1250 $\mu$L per second from the three nozzles in the transfer device. The disposable was moved on the timing belt to allow subsequent well pairs to be located under the transfer device and to affect transfer of the reaction mixture. The disposable device was then moved to a read position, where a chemiluminescence read head (as described by a co-owned and co-pending application by Khalil et al ser. No. 16,936) was lowered to mate with the surface feature on the first two wells on the disposable to create a light-tight seal. The retained and immobilized immune complex on the pad was triggered using 0.3% alkaline peroxide solution and the signal was integrated for eight seconds. The measured signal for each well was considered to correspond to the amount of acridinium labeled conjugate attached to the fibrous pad surface by ionic forces.

TABLE 4

Ion-Capture Competitive Binding Assay For Phenylcyclidine (PCP) in Urine

| PCP [ng/ml] | Side A | | Side B | |
| --- | --- | --- | --- | --- |
| | Signal | % Bound | Signal | % Bound |
| 0 | 199886 | 0.00 | 181430 | 00.00 |
| 25 | 33752 | 83.00 | 27753 | 85.50 |
| 60 | 12412 | 94.6 | 12140 | 94.19 |
| 120 | 6818 | 97.44 | 6106 | 97.54 |
| 250 | 3223 | 99.28 | 2907 | 99.32 |
| 500 | 1803 | 100.00 | 1690 | 10000 |

The cut-off of this assay is considered at 25 ng/ml. The data indicate that Percent bound figures in Table 4 show that all controls containing 25 ng/ml PCP or higher were well differentiated from the negative control which indicates the validity of the fluid transfer and show that transfer of reaction mixture and washing of porous matrix was affected using the method and device of the present invention.

Although the present invention has been described in terms of preferred embodiment, it is anticipated that various modifications and improvements will occur to those skilled in the art upon consideration of the present invention. Thus, shape, material and color of the vessel, material of the porous matrix, material and shape and number of layers of absorbant pad; Different angles of injection, shape of injectors, speed of injection, and type and composition of was solution; Treatment of fibrous pad to decrease non-specific binding can all be optimized by those skilled in the art. The device and method of this invention can be used to perform immunoassays for macromolecular antigens, viral and bacterial antigens and haptens. It can be extended to nucliec acid probes. Although the invention has been described using acridinium sulfonamide labeled tracers, it can be extended to other acridinium compounds or their analogs. Other kinds of chemiluminescence can be performed and detected using the device and method of this invention such as luminol type chemiluminescence or enzyme catalyzed dioxetane chemiluminescence. Further the device and method of this invention can be used with other detection methods and hence with other labels; thus front surface measurements using enzyme catalyzed substrate fluorescence or time resolved fluorescence and rare earth chelate labels or pripitated product immunoassays and reflectance measurements.

We claim:

1. A device suitable for performing a plurality of automated solid-phase diagnostic assays, said device comprising a plurality of elements each comprising:
   a sample well for receiving a sample and reagents for forming a reaction mixture which produces a detectable reaction product corresponding to an analyte in said sample;
   a read well positioned adjacent to said sample well comprising:
   (a) an entrance port and holding means for receiving and holding said reaction mixture from said sample well;
   (b) a fibrous matrix for immobilizing said reaction product for detection thereof, said fibrous matrix positioned below and in fluid communication with said holding means, and having an average separation of fibers to allow free flow of said reaction mixture;
   (c) an absorbent material positioned below and in fluid communication with said fibrous matrix to absorb any sample or assay reagents that flow through said fibrous matrix;
   means for venting air entrapped in the absorbent material and displaced by fluids absorbed therein; and
   passage means communicating between said sample well and said read well such that when wash fluid is injected into said sample well said reaction mixture is washed from said sample well through said passage means into said read well.

2. The device of claim 1, wherein said fibrous matrix has an average spatial separation of fibers greater than 10 microns.

3. The device of claim 1, wherein said plurality of elements are in the form of a two by eight array.

4. The device of claim 1, wherein each read well has an individual fibrous matrix.

5. The device of claim 1, wherein said absorbant material is common to all read wells.

6. The device of claim 1, wherein said absorbant material is held securely in contact with said fibrous matrix by positioning means.

7. The device of claim 1, wherein said sample well is concave with a largest radius of curvature along an axis connecting said sample well to said passage means.

8. The device of claim 1, wherein each said element further comprises a means for creating a substantially light-tight seal comprising a wall surrounding each said element, said means for creating a light-tight seal being matable with a signal reader having a matching groove padded with compressible polymeric material.

9. The device of claim 8, wherein adjacent elements share a common wall.

* * * * *

UNITED STATES PATENT AND TRADEMARK OFFICE
CERTIFICATE OF CORRECTION

PATENT NO. : 5,244,630                                   Page 1 of 2
DATED : September 14, 1993
INVENTOR(S) : O.S. Khalil et al.

It is certified that error appears in the above-indentified patent and that said Letters Patent is hereby corrected as shown below:

Column 1, line 59, change "which reads with" to -- which reacts with --.

Column 3, line 51, change "mechanically transfer" to -- mechanical transfer --.

Column 11, line 17, change "form the microparticles" to -- form the microparticle --.

Column 11, line 51, change "Celquat TM L-200" to -- Celquat$^{TM}$ L-200 --.

Column 11, line 54, change " labeled anti body" to -- labeled antibody --.

Column 11, line 56, change " bound to a an" to -- bound to an --.

Column 13, line 2, change "0.0250-0.1% Tween®," to -- 0.0250-0.1% Tween®-20, --.

Column 13, line 17, change " or Hepatites B core" to -- to Hepatites B core --.

UNITED STATES PATENT AND TRADEMARK OFFICE
CERTIFICATE OF CORRECTION

PATENT NO. : 5,244,630
DATED : September 14, 1993
INVENTOR(S) : O.S. Khalil et al.

It is certified that error appears in the above-indentified patent and that said Letters Patent is hereby corrected as shown below:

Column 15, lin 59, change " between the to " to -- between the two --.

Column 17, line 39, change "device and and tan" to -- device and tan --.

Column 17, line 49, change "Celquat TM L-200" to -- Celquat$^{TM}$ L-200 --.

Column 18, line 34, change " TDx TM" to -- TDx$^{TM}$ --.

Signed and Sealed this

Twelfth Day of April, 1994

Attest:

BRUCE LEHMAN

*Attesting Officer*   *Commissioner of Patents and Trademarks*